(12) United States Patent
Amin et al.

(10) Patent No.: US 9,731,998 B2
(45) Date of Patent: Aug. 15, 2017

(54) ANTIMICROBIAL GLASS ARTICLES WITH IMPROVED STRENGTH AND METHODS OF MAKING AND USING SAME

(71) Applicant: CORNING INCORPORATED, Corning, NY (US)

(72) Inventors: Jaymin Amin, Corning, NY (US); Timothy Michael Gross, Corning, NY (US); Odessa Natalie Petzold, Elmira, NY (US); Rostislav Vatchev Roussev, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 15/178,940

(22) Filed: Jun. 10, 2016

(65) Prior Publication Data

US 2016/0280592 A1 Sep. 29, 2016

Related U.S. Application Data

(62) Division of application No. 14/288,749, filed on May 28, 2014.

(Continued)

(51) Int. Cl.
*B32B 15/04* (2006.01)
*B32B 17/06* (2006.01)
(Continued)

(52) U.S. Cl.
CPC ............ *C03C 21/005* (2013.01); *A01N 59/16* (2013.01); *C03C 3/091* (2013.01); *C03C 3/097* (2013.01);
(Continued)

(58) Field of Classification Search
USPC ....... 428/409, 410, 426, 432, 433, 434, 688, 428/689, 697, 701, 702; 65/30.14
See application file for complete search history.

(56) References Cited

U.S. PATENT DOCUMENTS

| 3,549,344 A | 12/1970 | Loukes et al. |
| 3,798,013 A | 3/1974 | Inoue et al. |

(Continued)

FOREIGN PATENT DOCUMENTS

| CN | 102388002 A | 3/2012 |
| DE | 102005039298 | 2/2007 |

(Continued)

OTHER PUBLICATIONS

Allan et al., U.S. Appl. No. 61/835,722, Methods of Characterizing the Ion Concentration in Double Ion-Exchanged Glasses, filed Jun. 17, 2013.

(Continued)

*Primary Examiner* — Lauren R Colgan
(74) *Attorney, Agent, or Firm* — Jie Gao

(57) ABSTRACT

Described herein are various antimicrobial glass articles that have improved strength and resistance to discoloration. The improved antimicrobial glass articles described herein generally include a glass substrate with a compressive stress layer and an antimicrobial silver-containing region that each extend inward from a surface of the glass substrate to a specific depth. In some embodiments, the compressive stress layer has a compressive stress at the surface of about 500 MPa or greater and the compressive stress decreases monotonically from the surface into the depth of the glass substrate. Methods of making and using the glass articles are also described and include forming a compressive stress layer and forming an antimicrobial silver-containing region by preferentially exchanging a plurality of silver cations in (Continued)

a silver-containing medium for a specific plurality of first cations ions in the glass substrate.

11 Claims, 5 Drawing Sheets

Related U.S. Application Data

(60) Provisional application No. 61/835,844, filed on Jun. 17, 2013.

(51) Int. Cl.
| | |
|---|---|
| C03C 21/00 | (2006.01) |
| C03C 3/097 | (2006.01) |
| A01N 59/16 | (2006.01) |
| C03C 3/091 | (2006.01) |
| C03C 4/18 | (2006.01) |

(52) U.S. Cl.
CPC .............. *C03C 4/18* (2013.01); *C03C 21/001* (2013.01); *C03C 21/002* (2013.01); *C03C 2204/02* (2013.01); *Y10T 428/315* (2015.01)

(56) References Cited

U.S. PATENT DOCUMENTS

| | | | |
|---|---|---|---|
| 5,078,772 A | 1/1992 | Asahara et al. | |
| 5,151,958 A | 9/1992 | Honkanen | |
| 7,232,777 B1 | 6/2007 | Van Hyning | |
| 8,232,218 B2 | 7/2012 | Dejneka et al. | |
| 8,312,739 B2 | 11/2012 | Lee et al. | |
| 8,561,429 B2 | 10/2013 | Allan et al. | |
| 8,586,492 B2 | 11/2013 | Barefoot et al. | |
| 8,969,226 B2 | 3/2015 | Dejneka et al. | |
| 8,973,401 B2 | 3/2015 | Borrelli et al. | |
| 9,156,724 B2 | 10/2015 | Gross | |
| 9,284,218 B1 | 3/2016 | Mauro et al. | |
| 9,346,703 B2 | 5/2016 | Bookbinder et al. | |
| 2008/0063728 A1 | 3/2008 | Fechner et al. | |
| 2009/0142568 A1 | 6/2009 | Dejneka et al. | |
| 2009/0220761 A1 | 9/2009 | Dejneka et al. | |
| 2010/0009154 A1* | 1/2010 | Allan .................. C03C 3/085 428/220 | |
| 2010/0028607 A1* | 2/2010 | Lee ..................... C03C 3/093 428/156 | |
| 2010/0035038 A1 | 2/2010 | Barefoot et al. | |
| 2010/0071415 A1 | 3/2010 | Voss et al. | |
| 2011/0267698 A1 | 11/2011 | Guilfoyle et al. | |
| 2011/0293942 A1 | 12/2011 | Cornejo et al. | |
| 2011/0294649 A1* | 12/2011 | Gomez ................ C03C 21/001 501/66 | |
| 2012/0034435 A1* | 2/2012 | Borrelli ................ C03C 17/30 428/210 | |
| 2012/0048604 A1 | 3/2012 | Cornejo et al. | |
| 2012/0052271 A1 | 3/2012 | Gomez et al. | |
| 2012/0171497 A1* | 7/2012 | Koyama ............... C03C 3/085 428/428 | |
| 2012/0216569 A1* | 8/2012 | Allan .................. C03C 21/002 65/30.14 | |
| 2012/0219792 A1 | 8/2012 | Yamamoto et al. | |
| 2013/0011650 A1* | 1/2013 | Akiba .................. C03C 3/085 428/220 | |
| 2013/0045375 A1 | 2/2013 | Gross | |
| 2013/0130023 A1 | 5/2013 | Boulanger et al. | |
| 2013/0219965 A1 | 8/2013 | Allan et al. | |
| 2013/0224492 A1 | 8/2013 | Bookbinder et al. | |
| 2014/0017500 A1* | 1/2014 | Koike ................... C03C 3/085 428/410 | |
| 2014/0066285 A1* | 3/2014 | Beall ................... C03B 20/00 501/32 | |
| 2014/0092377 A1 | 4/2014 | Liu et al. | |
| 2014/0099501 A1* | 4/2014 | Yamamoto ............. C03C 3/085 428/335 | |
| 2014/0118740 A1 | 5/2014 | Fontaine et al. | |
| 2014/0227524 A1 | 8/2014 | Ellison et al. | |
| 2014/0345325 A1* | 11/2014 | Allan .................... C03C 21/002 65/30.14 | |
| 2014/0356405 A1 | 12/2014 | Neff et al. | |
| 2014/0356406 A1 | 12/2014 | Patil et al. | |
| 2014/0356605 A1 | 12/2014 | Adib et al. | |
| 2014/0370302 A1 | 12/2014 | Amin et al. | |
| 2014/0370303 A1* | 12/2014 | Jin ....................... C03C 21/005 428/426 | |
| 2015/0044445 A1 | 2/2015 | Garner et al. | |
| 2015/0044473 A1* | 2/2015 | Murata ................. C03C 3/083 428/410 | |
| 2015/0147538 A1* | 5/2015 | Ishimaru ............... C03C 21/002 428/192 | |
| 2015/0147574 A1 | 5/2015 | Allan et al. | |
| 2015/0147576 A1 | 5/2015 | Bookbinder et al. | |
| 2015/0147775 A1 | 5/2015 | Fiacco et al. | |
| 2015/0211090 A1 | 7/2015 | Johnson et al. | |
| 2015/0211091 A1 | 7/2015 | Johnson et al. | |
| 2015/0239777 A1 | 8/2015 | Mauro | |
| 2015/0307961 A1 | 10/2015 | Johnson et al. | |

FOREIGN PATENT DOCUMENTS

| | | |
|---|---|---|
| EP | 250635 | 12/1990 |
| EP | 1270527 A1 | 1/2003 |
| EP | 2021296 A1 | 2/2009 |
| EP | 2064220 | 10/2010 |
| EP | 1828071 | 2/2011 |
| JP | 1999319042 | 11/1999 |
| JP | 2000053451 A | 2/2000 |
| JP | 200180941 | 3/2001 |
| JP | 2010138025 A | 6/2010 |
| JP | 2011133800 A | 7/2011 |
| JP | 04916503 B2 | 4/2012 |
| JP | 2012079133 | 4/2012 |
| KR | 1268956 | 5/2013 |
| WO | 2006058906 | 6/2006 |
| WO | 2011065293 | 6/2011 |
| WO | 2011069338 | 6/2011 |
| WO | 2012019067 A1 | 2/2012 |
| WO | WO2012124757 | * 9/2012 |
| WO | WO2012128180 | * 9/2012 |
| WO | WO2013176150 | * 11/2013 |

OTHER PUBLICATIONS

Patent Cooperation Treaty International Notification of Transmittal of the International Search Report and The Written Opinion of the International Searching Authority, international application No. PCT/US2014/042653: mailing date Dec. 16, 2015, 9 pages.

* cited by examiner

ANTIMICROBIAL GLASS ARTICLES WITH IMPROVED STRENGTH AND METHODS OF MAKING AND USING SAME

This application is a divisional of U.S. application Ser. No. 14/288,749, filed May 28, 2014, which claims the benefit of priority under 35 U.S.C. §119 of U.S. Provisional Application Ser. No. 61/835,844 filed on Jun. 17, 2013, the contents of which are relied upon and incorporated herein by reference in its entirety.

BACKGROUND

The present disclosure relates generally to antimicrobial glass articles. More particularly, the various embodiments described herein relate to glass articles having antimicrobial behavior and improved strength, as well as to methods of making and using the glass articles.

Touch-activated or -interactive devices, such as screen surfaces (e.g., surfaces of electronic devices having user-interactive capabilities that are activated by touching specific portions of the surfaces), have become increasingly more prevalent. In general, these surfaces should exhibit high optical transmission, low haze, and high durability, among other features. As the extent to which the touch screen-based interactions between a user and a device increases, so too does the likelihood of the surface harboring microorganisms (e.g., bacteria, fungi, viruses, and the like) that can be transferred from user to user.

To minimize the presence of microbes on glass, so-called "antimicrobial" properties have been imparted to a variety of glass articles. Such antimicrobial glass articles, regardless of whether they are used as screen surfaces of touch-activated devices or in other applications, still need to exhibit high strength (including high average flexural strength). In addition, such antimicrobial articles should also be resistant to color changes when exposed to elevated temperatures, humidity, reactive environments and the like. These harsh conditions can occur during fabrication or processing of the glass articles, or during ordinary use of the articles. In certain cases, this discoloration can render a glass article unsightly. Further, excessive discoloration ultimately can lead to the glass article becoming unsuitable for its intended purpose.

There accordingly remains a need for technologies that provide antimicrobial glass articles with improved strength and resistance against discoloration when exposed to harsh conditions.

BRIEF SUMMARY

Described herein are various antimicrobial glass articles that have improved strength and resistance to discoloration when exposed to harsh conditions, along with methods for their manufacture and use.

One type of improved antimicrobial glass article includes a glass substrate that has a compressive stress layer or region that extends inward from a surface of the glass substrate to a first depth and an antimicrobial silver-containing layer or region that extends inward from the surface of the glass substrate to a second depth, which may, optionally, be less than the first depth. In one or more embodiments, the compressive stress layer comprises a compressive stress at the surface of the glass substrate of about 500 megapascals (MPa) or greater. The upper limit of the compressive stress may be about 1.2 gigapascals (GPa). The depth of the compressive stress layer may be less than about 100 micrometers ($\mu$m). In some embodiments, the compressive stress decreases monotonically from the surface into the depth of the glass substrate.

In one or more embodiments, the antimicrobial silver-containing region may have a depth of about 20 $\mu$m or less or about 10 $\mu$m or less. In some instances, the antimicrobial silver-containing region has a silver concentration of about 6 weight percent or greater, based on a total weight of the antimicrobial silver-containing region. The silver concentration at an outermost 0.01 $\mu$m or 10 nanometers (nm) of the antimicrobial silver-containing region may be up to about 45 weight percent, based on a total weight of this outermost 10 nm of the antimicrobial silver-containing region. In some instances, the concentration at this outermost 10 nm of the antimicrobial silver-containing region may be up to about 6 weight percent, based on the total weight of this outermost 10 nanometers of the antimicrobial silver-containing region.

In one or more alternative embodiments, the antimicrobial silver-containing region may be thicker. For example, the antimicrobial silver-containing region may have a thickness of up to about 150 $\mu$m (e.g., in the range from about 20 $\mu$m to about 150 $\mu$m).

The antimicrobial glass article may include an additional layer disposed on the surface of the glass substrate. Examples of the additional layer include a reflection-resistant coating, a glare-resistant coating, fingerprint-resistant coating, smudge-resistant coating, a color-providing composition, an environmental barrier coating, and an electrically conductive coating.

The antimicrobial glass article may exhibit at least a 5 log reduction in a concentration of at least *Staphylococcus aureus, Enterobacter aerogenes*, and *Pseudomonas aeruginosa* bacteria under JIS Z 2801 (2000) testing conditions. In some cases, the antimicrobial glass article may exhibit at least a 3 log reduction in a concentration of at least *Staphylococcus aureus, Enterobacter aerogenes*, and *Pseudomonas aeruginosa* bacteria under modified JIS Z 2801 (2000) testing conditions, wherein the modified conditions comprise heating the antimicrobial glass article to a temperature of about 23 degrees Celsius to about 37 degrees Celsius at a relative humidity of about 38 percent to about 42 percent for about 24 hours followed by drying for about 6 hours to about 24 hours. In yet other embodiments, the antimicrobial glass article may exhibit at least a 2 log reduction in the concentration of at least *Staphylococcus aureus, Enterobacter aerogenes*, and *Pseudomonas aeruginosa* bacteria under a Dry Test.

Embodiments of the antimicrobial glass article may be included as at least a portion of a touch-sensitive display screen or cover plate for an electronic device, a non-touch-sensitive component of an electronic device, a surface of a household appliance, a surface of medical equipment, a biological or medical packaging vessel, or a surface of a vehicle component.

Methods of making the antimicrobial glass articles described herein are also provided. In one or more embodiments, the method includes providing a glass substrate, forming a compressive stress layer that extends inward from a surface of the glass substrate to a first depth, and forming an antimicrobial silver-containing region that extends inward from the surface of the glass substrate to a second depth. In one or more embodiments, forming the antimicrobial silver-containing region can include exchanging a plurality of silver cations in a silver-containing medium for a plurality of first cations in the glass substrate. In some embodiments, forming the compressive layer includes immersing the glass substrate in a molten salt bath comprising a poisoning component, which may be present in an amount in the range from about 0.01 wt % to about 10 wt %, based on the total weight of the molten salt bath.

The poisoning component can include at least one of a cation having an ionic radius that is smaller than the ionic radius of a potassium cation, and a cation that is identical to the first cation in the glass substrate. Examples of the poisoning component include $NaNO_3$ and $LiNO_3$. In one or more embodiments, the plurality of first cations is present in the glass substrate before or after forming the compressive stress layer. Accordingly, in one or more embodiments, the method may include introducing the plurality of first cations into the glass substrate before forming the antimicrobial silver-containing region.

In one or more alternative embodiments, the step of forming the compressive stress layer and the step of forming the antimicrobial silver-containing region occur simultaneously.

It is to be understood that both the foregoing brief summary and the following figures and detailed description describe various embodiments and are intended to provide an overview or framework for understanding the nature and character of the claimed subject matter.

DETAILED DESCRIPTION

Figure 1:
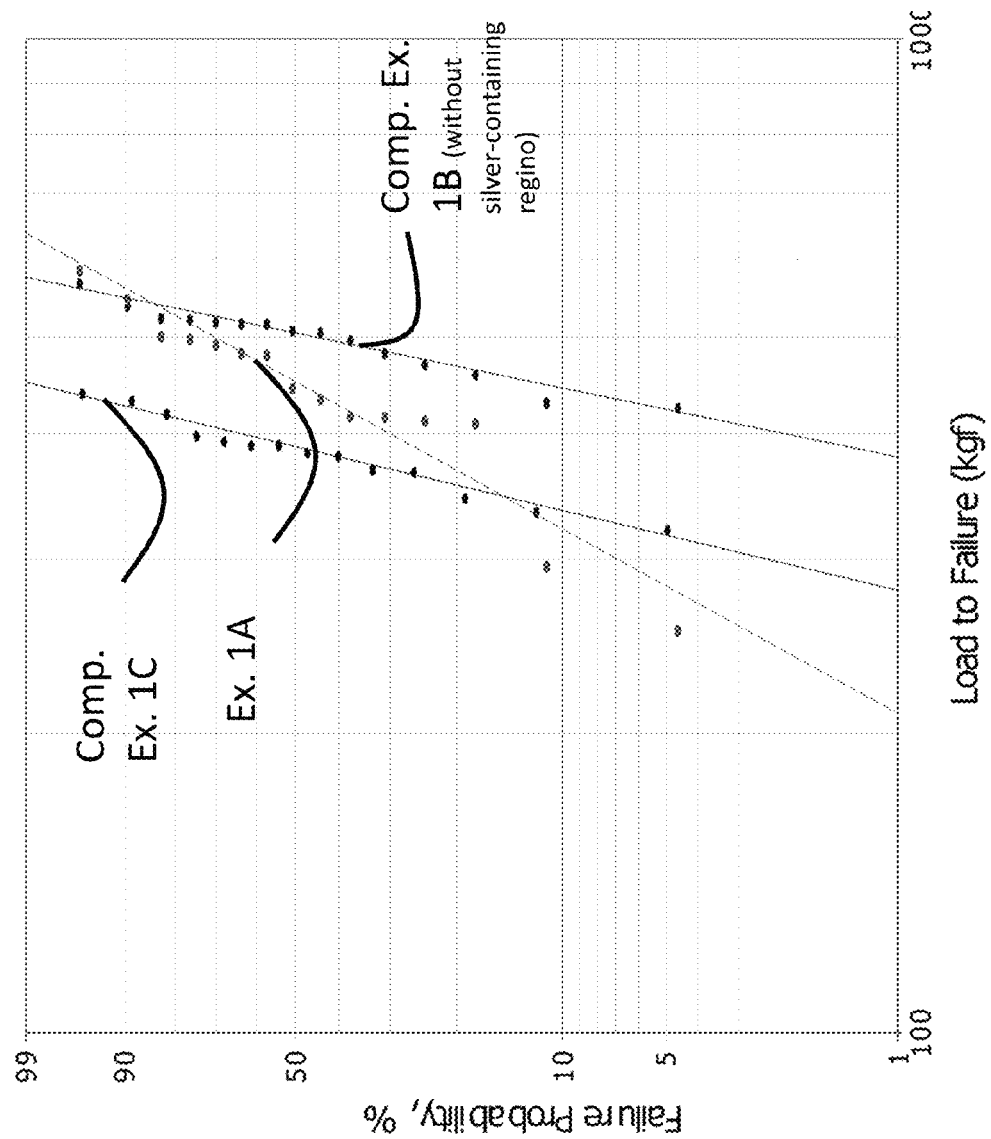
FIG. 1 is a Weibull plot showing the strength distributions, as measured by ring-on-ring testing, of Example 1A and Comparative Examples 1B-1C.

Referring now to the figures, wherein like reference numerals represent like parts throughout the several views, exemplary embodiments will be described in detail. Throughout this description, various components may be identified having specific values or parameters. These items, however, are provided as being exemplary of the present disclosure. Indeed, the exemplary embodiments do not limit the various aspects and concepts, as many comparable parameters, sizes, ranges, and/or values may be implemented. Similarly, the terms "first," "second," "primary," "secondary," "top," "bottom," "distal," "proximal," and the like, do not denote any order, quantity, or importance, but rather are used to distinguish one element from another. Further, the terms "a," "an," and "the" do not denote a limitation of quantity, but rather denote the presence of "at least one" of the referenced item.

Described herein are various antimicrobial glass articles that have improved strength and resistance to discoloration when exposed to harsh conditions (i.e., during manufacture and/or use of the articles), along with methods for their manufacture and use. The term "antimicrobial" refers herein to the ability to kill or inhibit the growth of more than one species of more than one type of microbe (e.g., bacteria, viruses, fungi, and the like).

The improved antimicrobial glass articles described herein generally include a glass substrate that has a compressive stress layer or region that extends inward from a surface of the glass substrate to a first depth, and an antimicrobial silver-containing layer or region that extends inward from a surface of the glass substrate to a second depth. Throughout this specification, the term "compressive stress layer" shall be used to refer to the layer or region of compressive stress, and the term "antimicrobial silver-containing region" shall be used to refer to the layer or region containing the antimicrobial silver species. This usage is for convenience only, and is not intended to provide a distinction between the terms "region" or "layer" in any way.

In general, the improved articles and methods described herein include a high concentration of silver along a relatively shallow depth of the glass substrate and which includes a compressive stress layer with a high compressive stress at the surface of the glass substrate. In some instances, the compressive stress decreases from the surface of the glass substrate along the compressive stress layer, monotonically. As used herein, the term "monotonically" or "monotonic" when used to describe the compressive stress means that the compressive stress decreases along the compressive stress layer from the surface of the glass substrate to the depth of the compressive stress layer (DOL) and does not increase by more than about 5 MPa at any location or locations along the compressive stress layer.

Glass Substrate

The choice of glass used for the glass substrate is not limited to a particular composition. For example, the composition chosen can be any of a wide range of silicate, borosilicate, aluminosilicate, or boroaluminosilicate glass compositions, which optionally can comprise one or more alkali and/or alkaline earth modifiers.

By way of illustration, one family of compositions includes those having at least one of aluminum oxide or boron oxide and at least one of an alkali metal oxide or an alkali earth metal oxide, wherein $-15$ mol $\% \leq (R_2O+R'O-Al_2O_3-ZrO_2)-B_2O_3 \leq 4$ mol %, where R can be Li, Na, K, Rb, and/or Cs, and R' can be Mg, Ca, Sr, and/or Ba. One subset of this family of compositions includes from about 62 mol % to about 70 mol % $SiO_2$; from 0 mol % to about 18 mol % $Al_2O_3$; from 0 mol % to about 10 mol % $B_2O_3$; from 0 mol % to about 15 mol % $Li_2O$; from 0 mol % to about 20 mol % $Na_2O$; from 0 mol % to about 18 mol % $K_2O$; from 0 mol % to about 17 mol % MgO; from 0 mol % to about 18 mol % CaO; and from 0 mol % to about 5 mol % $ZrO_2$. Such glasses are described more fully in U.S. patent application Ser. No. 12/277,573 by Matthew J. Dejneka et al., entitled "Glasses Having Improved Toughness And Scratch Resistance," filed Nov. 25, 2008, and claiming priority to U.S. Provisional Patent Application No. 61/004,677, filed on Nov. 29, 2008, the contents of which are incorporated herein by reference in their entireties as if fully set forth below.

Another illustrative family of compositions includes those having at least 50 mol % $SiO_2$ and at least one modifier selected from the group consisting of alkali metal oxides and alkaline earth metal oxides, wherein $[(Al_2O_3 \text{ (mol \%)}+B_2O_3 \text{ (mol \%)})/(\Sigma \text{ alkali metal modifiers (mol \%)})] > 1$. One subset of this family includes from 50 mol % to about 72 mol % $SiO_2$; from about 9 mol % to about 17 mol % $Al_2O_3$; from about 2 mol % to about 12 mol % $B_2O_3$; from about 8 mol % to about 16 mol % $Na_2O$; and from 0 mol % to about 4 mol % $K_2O$. Such glasses are described in more fully in U.S. patent application Ser. No. 12/858,490 by Kristen L. Barefoot et al., entitled "Crack And Scratch Resistant Glass and Enclosures Made Therefrom," filed Aug. 18, 2010, and claiming priority to U.S. Provisional Patent Application No.

61/235,767, filed on Aug. 21, 2009, the contents of which are incorporated herein by reference in their entireties as if fully set forth below.

Yet another illustrative family of compositions includes those having $SiO_2$, $Al_2O_3$, $P_2O_5$, and at least one alkali metal oxide ($R_2O$), wherein $0.75 \leq [P_2O_5(\text{mol \%}) + R_2O(\text{mol \%})]/M_2O_3 \text{ (mol \%)}] \leq 1.2$, where $M_2O_3 = Al_2O_3 + B_2O_3$. One subset of this family of compositions includes from about 40 mol % to about 70 mol % $SiO_2$; from 0 mol % to about 28 mol % $B_2O_3$; from 0 mol % to about 28 mol % $Al_2O_3$; from about 1 mol % to about 14 mol % $P_2O_5$; and from about 12 mol % to about 16 mol % $R_2O$. Another subset of this family of compositions includes from about 40 to about 64 mol % $SiO_2$; from 0 mol % to about 8 mol % $B_2O_3$; from about 16 mol % to about 28 mol % $Al_2O_3$; from about 2 mol % to about 12 mol % $P_2O_5$; and from about 12 mol % to about 16 mol % $R_2O$. Such glasses are described more fully in U.S. patent application Ser. No. 13/305,271 by Dana C. Bookbinder et al., entitled "Ion Exchangeable Glass with Deep Compressive Layer and High Damage Threshold," filed Nov. 28, 2011, and claiming priority to U.S. Provisional Patent Application No. 61/417,941, filed Nov. 30, 2010, the contents of which are incorporated herein by reference in their entireties as if fully set forth below.

Yet another illustrative family of compositions includes those having at least about 4 mol % $P_2O_5$, wherein $(M_2O_3 \text{ (mol \%)}/R_xO \text{ (mol \%)}) < 1$, wherein $M_2O_3 = Al_2O_3 + B_2O_3$, and wherein $R_xO$ is the sum of monovalent and divalent cation oxides present in the glass. The monovalent and divalent cation oxides can be selected from the group consisting of $Li_2O$, $Na_2O$, $K_2O$, $Rb_2O$, $Cs_2O$, MgO, CaO, SrO, BaO, and ZnO. One subset of this family of compositions includes glasses having 0 mol % $B_2O_3$. Such glasses are more fully described in U.S. Provisional Patent Application No. 61/560,434 by Timothy M. Gross, entitled "Ion Exchangeable Glass with High Crack Initiation Threshold," filed Nov. 16, 2011, the contents of which are incorporated herein by reference in their entirety as if fully set forth below.

Still another illustrative family of compositions includes those having $Al_2O_3$, $B_2O_3$, alkali metal oxides, and contains boron cations having three-fold coordination. When ion exchanged, these glasses can have a Vickers crack initiation threshold of at least about 30 kilograms force (kgf). One subset of this family of compositions includes at least about 50 mol % $SiO_2$; at least about 10 mol % $R_2O$, wherein $R_2O$ comprises $Na_2O$; $Al_2O_3$, wherein $-0.5$ mol $\% \leq Al_2O_3(\text{mol \%}) - R_2O(\text{mol \%}) \leq 2$ mol %; and $B_2O_3$, and wherein $B_2O_3$ (mol %) − ($R_2O$(mol %) − $Al_2O_3$(mol %)) ≥ 4.5 mol %. Another subset of this family of compositions includes at least about 50 mol % $SiO_2$, from about 9 mol % to about 22 mol % $Al_2O_3$; from about 4.5 mol % to about 10 mol % $B_2O_3$; from about 10 mol % to about 20 mol % $Na_2O$; from 0 mol % to about 5 mol % $K_2O$; at least about 0.1 mol % MgO and/or ZnO, wherein 0≤MgO+ZnO≤6 mol %; and, optionally, at least one of CaO, BaO, and SrO, wherein 0 mol %≤CaO+SrO+BaO ≤2 mol %. Such glasses are more fully described in U.S. Provisional Patent Application No. 61/653,485 by Matthew J. Dejneka et al., entitled "Ion Exchangeable Glass with High Damage Resistance," filed May 31, 2012, the contents of which are incorporated herein by reference in their entirety as if fully set forth below.

In one or more embodiments, the glass substrate may include a low concentration of nonbridging oxygens (NBOs). As used herein, the term "nonbridging oxygens" is intended to refer to those oxygen atoms within the glass that bear a negative charge that can be compensated by a vicinal positively charged ion. For example, where silicon is bonded to four oxygen atoms and where the bond between the silicon atom and one of the oxygen atoms is broken, that oxygen atom bears a negative charge, which may be compensated by an alkali atom (e.g., Na). This is in contrast to those oxygen atoms within the glass that are covalently bonded to other atoms and do not bear a negative charge (such oxygen atoms being termed "bridging oxygens"). One way to determine the concentration of NBOs includes subtracting the sum of the concentrations, in mole percent (mol %), of all alkali metal oxides from the concentration, in mol %, of aluminum oxide. That is, NBO concentration is proportional to ($Al_2O_3$ (mol %)−(Σ alkali metal oxides (mol %)). It is important to note that, because of this particular NBO concentration calculation, NBO concentration values can be negative. Thus, in some implementations of the glass articles, the concentration of NBOs may be less than zero. Where the difference $Al_2O_3$ (mol %)−(Σ alkali metal oxides (mol %)) equals zero or a positive number, then there are no NBOs present. Where the difference $Al_2O_3$ (mol %)−(Σ alkali metal oxides (mol %)) equals a negative number, that negative number indicates the presence of NBOs.

In one or more embodiments, the glass substrate may have a low concentration of NBOs, In general, the concentration of NBOs, as defined above, in the glass articles can be, in mol %, ≥ to about −1, ≥ to about −0.9, ≥ to about −0.8, ≥ to about −0.7, ≥ to about −0.6, ≥ to about −0.5, ≥ to about −0.4, ≥ to about −0.3, ≥ to about −0.2, ≥ to about −0.1, ≥ to about 0, ≥ to about 0.1, ≥ to about 0.2, ≥ to about 0.3, ≥ to about 0.4, ≥ to about 0.5, ≥ to about 0.6, ≥ to about 0.7, ≥ to about 0.8, ≥ to about 0.9≥ to about 1. In some embodiments, the NBO concentration may be in the range from about −1 mol % to about 20 mol %, from about −1 mol % to about 15 mol %, from about −1 mol % to about 10 mol %, from about −1 mol % to about 5 mol %, from about −1 mol % to about 4 mol %, from about −1 mol % to about 3 mol %, from about −1 mol % to about 2 mol %, from about −1 mol % to about 1 mol %, from about −1 mol % to about 0.75 mol %, from about −1 mol % to about 0.5 mol %, from about −1 mol % to about 0.25 mol %, from about −1 mol % to about 0 mol %, from about −0.75 mol % to about 1 mol %, from about −0.5 mol % to about 1 mol %, from about −0.25 mol % to about 1 mol %, from about −0.25 mol % to about 0.25 mol % and all ranges and sub-ranges therebetween.

The glass substrate can adopt a variety of physical forms. That is, from a cross-sectional perspective, the substrate can be flat or planar, or it can be curved and/or sharply-bent. Similarly, it can be a single unitary object, or a multi-layered structure or a laminate.

There is no particular limitation on the average thickness of the glass substrate contemplated herein. In many exemplary applications, however the average thickness may be less than or equal to about 15 millimeters (mm) If the antimicrobial glass article is to be used in applications where it may be desirable to optimize thickness for weight, cost, and strength characteristics (e.g., in electronic devices, or the like), then even thinner substrates (e.g., less than or equal to about 5 mm) can be used. By way of example, if the antimicrobial glass article is intended to function as a cover for a touch screen display, then the substrate can exhibit an average thickness of about 0.02 mm to about 2.0 mm.

Antimicrobial Silver-Containing Region

The antimicrobial glass article of one or more embodiments includes an antimicrobial silver-containing layer or region that extends inward from a surface of the glass substrate to a specific depth therein. The antimicrobial silver-containing region comprises cationic monovalent silver (Ag$^+$) in an amount effective to impart antimicrobial behavior to the glass article. In general, the antimicrobial silver-containing region, like the compressive stress layer, extends inward from the surface of the glass substrate to a depth of the antimicrobial silver containing region (DOR). Thus the antimicrobial silver-containing region at least partially overlaps with the compressive stress layer. In some embodiments, the DOL is greater than the DOR. In one or more embodiments, the DOR may be generally limited to avoid visible coloration in the glass article and to maximize the antimicrobial efficacy of the cationic silver within the glass substrate. For example, the DOR may be about 20 μm or less. In some instances, the DOR may be in the range from about 0.1 μm to about 20 μm, from about 0.1 μm to about 18 μm, from about 0.1 μm to about 16 μm, from about 0.1 μm to about 14 μm, from about 0.1 μm to about 12 μm, from about 0.1 μm to about 10 μm, from about 0.1 μm to about 8 μm, from about 0.1 μm to about 5 μm, from about 1 μm to about 20 μm, from about 5 μm to about 20 μm, from about 6 μm to about 20 μm, from about 7 μm to about 20 μm, from about 8 μm to about 20 μm, from about 9 μm to about 20 μm, from about 10 μm to about 20 μm, from about 11 μm to about 20 μm, from about 12 μm to about 20 μm, from about 13 μm to about 20 μm, from about 14 μm to about 20 μm, from about 15 μm to about 20 μm, or from about 8 μm to about 15 μm, and all ranges and sub-ranges therebetween.

The DOR of the antimicrobial silver-containing region may be controlled to prevent or minimize discoloration of the glass substrate. As will be described herein, the method of forming the antimicrobial silver-containing region may be tailored to minimize the DOR of the antimicrobial silver-containing region, while still providing a high silver concentration at the surface (or along a select depth from the surface) of the glass substrate. Without being bound by theory, it is believed that the increased amount of silver at deeper depths of the glass substrate causes discoloration because at least a portion of the silver cations is reduced by electron donors in the glass (e.g., transition metals or NBOs). By reducing the diffusion of silver cations in the glass substrate and thus reducing the DOR of the antimicrobial silver-containing region, and maintaining a high surface concentration of silver, the propensity to discolor is reduced because silver reduction is minimized.

In certain implementations of the antimicrobial glass article, the antimicrobial silver-containing region can have a silver concentration in an outermost portion of such an antimicrobial silver-containing region of greater than about 5 weight percent and, in some cases, up to about 45 weight percent, based on the total weight of the antimicrobial silver-containing region. In some embodiments, the outermost portion of the antimicrobial silver-containing region may be from the surface of the antimicrobial glass article to a depth of about 0.01 μm. In some embodiments, the silver concentration in the outermost portion of the antimicrobial silver-containing region may be at least about 10 weight percent or greater, about 15 weight percent or greater, about 20 weight percent or greater, about 25 weight percent or greater or about 30 weight percent or greater. The upper limit of the silver concentration at the outermost portion may be about 40 weight percent. In some instances, the silver concentration may be in a range from about 15 weight percent to about 35 weight percent.

In other implementations, the antimicrobial silver-containing region can have an DOR of up to about 20 μm and, in some instances, in a range from about 0.01 μm to about 20 μm. A silver concentration in an outermost portion of such an antimicrobial silver-containing region (which includes about the outermost 0.01 μm or outermost 50 nm) can be up to about 6 weight percent.

In one or more alternative embodiments, the DOL and the DOR are about the same. In some specific alternative embodiments, the DOR may be greater than the DOL. In such embodiments, the DOR may be up to about 150 μm (e.g., in the range from about 20 μm to about 150 μm).

Compressive Stress Layer

The antimicrobial article of one or more embodiments includes a compressive stress layer or region that extends inward from a surface of the glass substrate to a specific depth therein. This compressive stress layer can be formed from a strengthening process (e.g., by thermal tempering, chemical ion-exchange, or like processes), as will be described in greater detail herein. The amount of compressive stress and the DOL can be varied based on the particular use for the glass article, with the proviso that the compressive stress and DOL should be limited such that a tensile stress created within the glass as a result of the compressive stress layer does not become so excessive as to render the glass article frangible. In one or more embodiments, the compressive stress at the surface of the glass substrate may be about 500 MPa or greater. In some embodiments, the compressive stress at the surface of the glass substrate may be in the range from about 500 MPa to about 1.2 GPa, from about 500 MPa, to about 1.1 GPa, from about 500 MPa to about 1 GPa, from about 500 MPa to about 950 MPa, from about 500 MPa to about 900 MPa, from about 500 MPa to about 850 MPa, from about 550 MPa to about 1.2 GPa, from about 600 MPa to about 1.2 GPa, from about 650 MPa to about 1.2 GPa, from about 700 MPa to about 1.2 GPa, from about 750 MPa to about 1.2 GPa, from about 800 MPa to about 1.2 GPa, from about 850 MPa to about 1.2 GPa, from about 500 MPa to about 900 MPa, from about 600 MPa to about 900 MPa, from about 700 MPa to about 900 MPa, and all ranges and sub-ranges therebetween. In one or more embodiments, the average compressive stress across the depth of the compressive stress layer generally may be between about 200 MP) and about 1.2 GPa). In most applications, the average compressive stress is greater than 400 MPa.

While the ultimate limit on the surface compressive and DOL is the avoidance of rendering the glass article frangible, the average DOL of the compressive stress layer generally may be less than about one-third of the thickness of the glass substrate. In most applications, however, the average DOL may be greater than or equal to about 25 μm and less than or equal to about 100 μm. In some instances, DOL can exceed 100 μm.

In one or more embodiments, the antimicrobial article includes a silver concentration in the outermost portion of the antimicrobial silver-containing region (e.g., outermost 0.01 μm of the antimicrobial silver-containing region) in the range from about 15 wt % to about 35 wt % and all ranges therebetween. Such articles may exhibit a surface CS in the range from about 450 MPa to about 900 MPa, or from about 450 MPa to about 800 MPa and all ranges and sub-ranges therebetween. In some examples, the articles exhibit an average flexural strength, as measured by ring-on-ring load to failure testing, as described herein, of about 250 kgf or greater. The antimicrobial articles of one or more embodiments exhibit at least a 15% improvement in surface CS over other antimicrobial articles that are not formed using a poisoning component, as described herein. In terms of average flexural strength, the antimicrobial articles of one or more embodiments exhibit at least a 4% or 9% improvement, and in some cases greater than about 40% improvement, in average flexural strength as measured by ring-on-ring load to failure, over other antimicrobial articles that are not formed using a poisoning component, as described herein.

In certain implementations, the antimicrobial glass articles can include an additional layer disposed on the surface of the glass substrate. The optional additional layer(s) can be used to provide additional features to the antimicrobial glass article (e.g., reflection resistance or anti-reflection properties, glare resistance or anti-glare properties, fingerprint resistance or anti-fingerprint properties, smudge resistance or anti-smudge properties, color, opacity, environmental barrier protection, electronic functionality, and/or the like). Materials that can be used to form the optional additional layer(s) generally are known to those skilled in the art to which this disclosure pertains.

Methods of making the above-described articles generally include the steps of providing a glass substrate, forming a compressive stress layer that extends inward from a surface of the glass substrate to a first depth, and forming an antimicrobial silver-containing region that extends inward from the surface of the glass substrate to a second depth. In those embodiments where the optional additional layer is implemented, the methods generally involve an additional step of forming the additional layer on at least a portion of the surface of the substrate.

The selection of materials used in the glass substrates and optional additional layers can be made based on the particular application desired for the final glass article. In general, however, the specific materials may be chosen from those described above.

Provision of the glass substrate can involve selection of a glass object as-manufactured, or it can entail subjecting the as-manufactured glass object to a treatment in preparation for any of the subsequent steps. Examples of such treatments include physical or chemical cleaning, physical or chemical etching, physical or chemical polishing, annealing, shaping, and/or the like.

Once the glass substrate has been selected and/or prepared, the compressive stress layer and/or the antimicrobial silver-containing region can be formed therein. That is, the compressive stress layer can be formed before, after, or simultaneously with the antimicrobial silver-containing region.

Formation of the compressive stress layer can be accomplished in a variety of ways, of which thermal tempering and chemical ion exchange are the most common. With thermal tempering, the glass substrate generally is heated above its annealing point, followed by a rapid cooling step to quench an outer or exterior region of the glass substrate in a compressed state, while an interior region of the glass cools at a slower rate and is placed under tension. The heating temperature, heating time, and cooling rate are generally the primary parameters that can be tailored to achieve a desired CS and DOL in the compressive stress layer (the exterior region of the glass substrate in a compressed state).

In contrast, with chemical ion exchange, the glass substrate is contacted with a molten salt bath (e.g., by dipping, immersing, spraying, or the like), during which smaller cations in the outer or exterior region of the glass substrate are replaced by, or exchanged with, larger cations of the same valence (usually $1^+$) from the molten salt bath to place the outer or exterior region under compression, while an interior region of the glass (in which no ion exchange occurs) is put under tension. Conditions such as contacting time, molten salt bath temperature, and salt concentration in the molten salt bath can be tailored to achieve a desired DOL and CS in the compressive stress layer (the exterior region in which the ion exchange occurs).

Similarly, the antimicrobial silver-containing region can be formed in a variety of ways, of which chemical diffusion (which optionally can be accompanied by the exchange of another cation out from the glass) of cationic silver from a silver-containing medium (e.g., paste, dispersion, ion exchange bath of molten salts, or the like) is the most common. In general, the glass substrate is contacted with the silver-containing medium (e.g., by dipping, immersing, spraying, or the like), and cationic silver diffuses from the silver-containing medium into an outer or exterior region of the glass substrate. In most situations, however, the cationic silver replaces, or exchanges with, another cations of the same valence (i.e., $1^+$) from the silver-containing medium. Conditions such as contacting time, silver-containing medium temperature, and silver concentration in the silver-containing medium can be tailored to achieve a desired DOR and silver concentration in the silver-containing region (the exterior region in which the cationic silver diffuses or ion exchanges).

In one or more embodiments, forming the compressive stress layer occurs before forming the antimicrobial silver-containing region. In some embodiments, the method includes forming the antimicrobial silver-containing region by exchanging a plurality of silver cations from the silver-containing medium for a plurality of specific or first cations from the glass substrate. In some embodiments, the first cations are present in the glass substrate before or after the compressive stress layer is formed. For example, in some embodiments, the glass substrate includes such first cations before forming the compressive stress layer and such first cations may include sodium, lithium or a combination thereof. In some embodiments, the first cations are introduced into the glass substrate when forming the compressive stress layer, and may be preset at or near the surface of the glass substrate where they may be available for exchange with other cations (e.g., silver cations). In such embodiments, the first cations may include sodium, lithium or a combination thereof, which are introduced into the glass substrate by immersing the glass substrate in a molten salt bath comprising a poisoning component. The molten salt bath may also include other salts used to form the compressive stress layer. The poisoning component of one or more alternative embodiments may also form compressive stress and thus the compressive stress layer in the glass substrate.

The poisoning component of one or more embodiments may include a cation that has an ionic radius that is smaller than the ionic radius of a potassium cation. In some embodiments, the poisoning component may be identical to the first cation in the glass substrate. Accordingly, the poisoning component of one or more embodiments may include a sodium cation, a lithium cation or a combination thereof.

The poisoning component may be present in the molten salt bath in an amount in the range from about 0.1 wt % to about 10 wt %, based on the total weight of the molten salt bath. In one or more embodiments, the poisoning component may be present in the molten salt bath in an amount in the range from about 0.1 wt % to about 10 wt %, about 0.1 wt % to about 9 wt %, about 0.1 wt % to about 8 wt %, about 0.1 wt % to about 7 wt %, about 0.1 wt % to about 6 wt %, about 0.1 wt % to about 5 wt %, about 0.1 wt % to about 4 wt %, about 0.1 wt % to about 3 wt %, about 0.1 wt % to about 2 wt %, about 1 wt % to about 10 wt %, about 2 wt % to about 10 wt %, about 3 wt % to about 10 wt %, about 4 wt % to about 10 wt %, about 5 wt % to about 10 wt %, about 3 wt % to about 7 wt %, about 4 wt % to about 6 wt %, and all ranges and sub-ranges therebetween, based on the total weight of the molten salt bath.

In one or more embodiments, the use of a poisoning component results in antimicrobial glass articles with improved strength due to preferential exchange of ions of similar size, and thus the formation of greater compressive stress (especially at the surface) in the glass articles as Ag+ ion-exchanges with Na+. The ionic radius of a sodium cation (Na+) is 116 picometers (μm), the ionic radius of a silver cation (Ag+) is 129 μm, and the ionic radius of a potassium cation (K+) is 153 μm.

In some known methods, the compressive stress layer is formed before the antimicrobial silver-containing region is formed. In such methods, the compressive stress layer is formed by immersing a glass substrate that includes a first cation (typically, Na+) in a molten salt bath of $KNO_3$. The exchange of K+ for Na+ in the glass substrate provides a compressive stress that is the greatest at the surface of the glass substrate, and extends through the compressive stress layer to the DOL. The compressive stress decreases monotonically along the compressive stress layer to the DOL. The antimicrobial silver-containing region is then formed and includes immersing the glass substrate with the compressive stress layer in a molten salt bath including K+ and Ag+ (typically $KNO_3$ and $AgNO_3$), and in some instances a third, non-exchanging salt. Ag+ exchanges preferentially for any Na+ remaining in the glass substrate, but where there is not enough Na+ in the glass substrate to exchange with both Ag+ and K+, Ag+ begins to exchange for the K+ that has been exchanged into the glass substrate due to the excess Ag+ entering the glass relative to Na+ available in the glass surface. The Ag+ that exchanges for K+ results in a decrease in compressive stress due to the much smaller ionic radius of Ag+ when compared to K+. The reduction in compressive stress may be pronounced at the surface of the glass substrate along the DOR of the antimicrobial silver-containing region.

Accordingly, the greater than concentration of Ag+ in an Ag+/K+ molten salt bath, the lower the resulting compressive stress from the surface to the diffusion depth (or DOL), as more Ag+ exchanges for K+ than Na+. A reduction in the amount of Ag+ in the Ag+/K+ molten salt bath to mitigate this effect means less silver in the antimicrobial silver-containing region, resulting in reduced antimicrobial efficacy or performance. An effect of an increased concentration of Ag+ in an Ag+/K+ molten salt bath includes a potential for higher silver contents at deeper penetration depth. In some instances, the Ag+ cations penetrate even deeper than K+ cations due to the smaller size of Ag+ cations. The deeper penetrated Ag+ cations can cause discoloration in the glass substrate.

The one or more embodiments of this disclosure, the method includes forming a compressive stress layer by immersing the glass substrate in a molten salt bath comprising a poisoning component. For example, the molten salt bath can include $KNO_3$ with a poisoning component including $NaNO_3$. By providing the poisoning component in the molten salt bath used to form the compressive stress layer, additional cations (such as Na+) are exchanged into the glass substrate, which are then present for exchange with Ag+ during formation of the antimicrobial silver-containing region. The method of one or more embodiments includes then forming the antimicrobial silver-containing region by immersing the glass substrate with the compressive stress layer for a much shorter time in a silver-containing medium (or silver-containing molten salt bath) having a lower temperature than the molten salt bath used to form the compressive stress layer. The Ag+ preferentially exchanges for the Na+ in the glass substrate with the compressive stress layer and thus exchange of Ag+ with K+ already exchanged into the glass substrate is reduced. Moreover, as Ag+ has a slightly larger ionic radius than Na+, the exchange of Ag+ for Na+ in the glass substrate increases the compressive stress in the glass substrate.

By way of example, one implementation of a method where the compressive stress layer is formed before the antimicrobial silver-containing region entails immersing the glass into a $KNO_3$-containing molten salt bath at a temperature of about 380 degrees Celsius (° C.) to about 460° C. for about 30 minutes to about 24 hours to impart the compressive stress via ion exchange, followed by immersing the strengthened glass into a $AgNO_3$-containing molten salt bath at a temperature of about 300° C. to about 400° C. for about 5 minutes to about 18 hours to ion exchange $Ag^+$ into the glass.

In such implementations, the $KNO_3$-containing molten salt bath can include $KNO_3$ and a poisoning component that undergoes ion exchange, and it can optionally include additional components that are inactive in the ion exchange process but aid, for example, in molten salt bath stability, pH control, viscosity control, or the like.

When the $KNO_3$-containing molten salt bath includes a poisoning component, suitable examples of the poisoning component can include $NaNO_3$ and $LiNO_3$, which may be used separately or in combination.

Similarly, in these implementations, the $AgNO_3$-containing molten salt bath can be formed entirely of $AgNO_3$. In some embodiments, the $AgNO_3$-containing molten salt bath can include $AgNO_3$ as the only active component that undergoes ion exchange, as well as additional components that are inactive in the ion exchange process but aid, for example, in molten salt bath stability, pH control, viscosity control, or the like. In some embodiments, the $AgNO_3$-containing molten salt bath can include $AgNO_3$ and a second or other active component that undergoes ion exchange, and it can optionally include additional components that are inactive in the ion exchange process but aid, for example, in molten salt bath stability, pH control, viscosity control, or the like.

When the $AgNO_3$-containing molten salt bath includes a second or other active component that undergoes ion exchange, the second active component generally may be $KNO_3$, in a concentration of about 75 wt % to about 99.95 wt %, based on the total weight of the $AgNO_3$-containing molten salt bath. In certain situations, the $AgNO_3$-containing molten salt bath can further include the poisoning component as a third active component (in addition to $KNO_3$ and $AgNO_3$) in an amount that is less than the amount of $AgNO_3$ in the $AgNO_3$-containing molten salt bath and/or less than or equal to the amount of the poisoning component in the $KNO_3$-containing molten salt bath of the compressive stress layer-forming step.

In one or more alternative embodiments, the compressive stress layer and the antimicrobial silver-containing region are formed simultaneously entails immersing the glass into a molten salt bath comprising both $KNO_3$ and $AgNO_3$ to ion exchange $K^+$ and $Ag^+$ into the glass together.

In such implementations, the $KNO_3$- and $AgNO_3$-containing molten salt bath can include $KNO_3$, $AgNO_3$, and a poisoning component that undergoes ion exchange, and it can optionally include additional components that are inactive in the ion exchange process but aid, for example, in molten salt bath stability, pH control, viscosity control, or the like.

After the compressive stress layer and the antimicrobial silver-containing region are formed, if desired, the optional additional layer(s) can be disposed on the surface of the glass substrate. Depending on the materials chosen, these coatings can be formed using a variety of techniques. For example, the optional additional layer(s) can be fabricated independently using any of the variants of chemical vapor deposition (CVD) (e.g., plasma-enhanced CVD, aerosol-assisted CVD, metal organic CVD, and the like), any of the variants of physical vapor deposition (PVD) (e.g., ion-assisted PVD, pulsed laser deposition, cathodic arc deposition, sputtering, and the like), spray coating, spin-coating, dip-coating, inkjetting, sol-gel processing, or the like. Such processes are known to those skilled in the art to which this disclosure pertains.

It should be noted that between any of the above-described steps, the glass substrate can undergo a treatment in preparation for any of the subsequent steps. As described above, examples of such treatments include physical or chemical cleaning, physical or chemical etching, physical or chemical polishing, annealing, shaping, and/or the like.

Once the glass article is formed, it can be used in a variety of applications where the article will come into contact with undesirable microbes. These applications encompass touch-sensitive display screens or cover plates for various electronic devices (e.g., cellular phones, personal data assistants, computers, tablets, global positioning system navigation devices, and the like), non-touch-sensitive components of electronic devices, surfaces of household appliances (e.g., refrigerators, microwave ovens, stovetops, oven, dishwashers, washers, dryers, and the like), medical equipment, biological or medical packaging vessels, and vehicle components, just to name a few devices.

Given the breadth of potential uses for the improved antimicrobial glass articles described herein, it should be understood that the specific features or properties of a particular article will depend on the ultimate application therefor or use thereof. The following description, however, will provide some general considerations.

As stated above, the thickness of the antimicrobial silver-containing region can be limited so as to avoid visible coloration in the glass article and to maximize the antimicrobial efficacy of the cationic silver within the glass substrate. The average thickness of the antimicrobial silver-containing region may be less than the DOL of the compressive stress layer. In some embodiments, as with the DOL of the compressive stress layer, the average thickness of the antimicrobial silver-containing region in one or more embodiments, may be less than about one-third of the thickness of the glass substrate. In some alternative embodiments, the average thickness of the antimicrobial silver-containing region may be up to about 100 µm, up to about 150 µm, up to about 300 µm, or up to the entire thickness of the glass substrate. The exact thickness, however, will vary depending on how the antimicrobial silver-containing region is formed.

For example, if the antimicrobial silver-containing region is formed before or after the compressive stress layer, and both are formed via chemical ion exchange, then the average thickness of the antimicrobial silver-containing region generally may be less than or equal to about 20 µm. In many such cases, the average thickness of the antimicrobial silver-containing region may be less than or equal to about 10 µm, less than or equal to about 5 µm, less than or equal to about 3 µm, less than or equal to about 2 µm, less than or equal to about 1 µm, or less than or equal to about 0.2 µm. The minimum average thickness of the antimicrobial silver-containing region may be about 10 nm. In some embodiments, the average thickness of the antimicrobial silver-containing region is in the range from about 5 micrometers (µm) to about 8 µm or from about 2 µm to about 5 µm. Within this antimicrobial silver-containing region, silver concentrations at the outermost portion of this region (which includes about the outermost 0.01 µm) of up to about 45 weight percent, based on the total weight of this portion of the region, can be attained.

In contrast, if the antimicrobial silver-containing region is formed at the same time as the compressive stress layer, and both are formed via chemical ion exchange, then the average thickness of the antimicrobial silver-containing region generally may be up to about 150 µm. In some embodiments, the average thickness of the antimicrobial silver-containing region may be in the range from about 20 µm to about 100 µm, from about 20 µm to about 150 µm or from about 20 µm to about 300 µm. Within this region, silver concentrations at the outermost portion of this region (which includes about the outermost 0.01 µm) of up to about 10 wt %, 9 wt %, 8 wt %, 7 wt %, 6 wt %, 5 wt %, 4 wt % or 3 wt %, based on the total weight of this portion of the region, can be attained.

When an optional additional layer is used, the average thickness of such a layer will depend on the function it serves. For example if a glare- and/or reflection-resistant layer is implemented, the average thickness of such a layer should be less than or equal to about 200 nm. Coatings that have an average thickness greater than this could scatter light in such a manner that defeats the glare and/or reflection resistance properties. Similarly, if a fingerprint- and/or smudge-resistant layer is implemented, the average thickness of such a layer should be less than or equal to about 100 nm.

In general, the optical transmittance of the antimicrobial glass article will depend on the type of materials chosen. For example, if a glass substrate is used without any pigments added thereto and/or any optional additional layers are sufficiently thin, the article can have a transparency over the entire visible spectrum of at least about 85%. In certain cases where the antimicrobial glass article is used in the construction of a touch screen for an electronic device, for example, the transparency of the antimicrobial glass article can be at least about 90% over the visible spectrum. In situations where the glass substrate comprises a pigment (or is not colorless by virtue of its material constituents) and/or any optional additional layers are sufficiently thick, the transparency can diminish, even to the point of being opaque across the visible spectrum. Thus, there is no particular limitation on the optical transmittance of the antimicrobial glass article itself.

Like transmittance, the haze of the antimicrobial glass article can be tailored to the particular application. As used herein, the terms "haze" and "transmission haze" refer to the percentage of transmitted light scattered outside an angular cone of ±4.0° in accordance with ASTM procedure D1003, the contents of which are incorporated herein by reference in their entirety as if fully set forth below. For an optically smooth surface, transmission haze is generally close to zero. In those situations when the antimicrobial glass article is used in the construction of a touch screen for an electronic device, the haze of the article can be less than or equal to about 5%, or more specifically, less than or equal to about 1%.

One or more of the embodiments of the antimicrobial glass articles described herein offer improved discoloration resistance to harsh conditions relative to existing antimicrobial glass articles. As used herein, the term "harsh conditions" refer to elevated temperatures, high relative humidities, reactive environments, and/or the like. For example, these can include temperatures of greater than about 180 degrees Celsius (° C.), relative humidities of greater than 50 percent (%), reducing environments, and/or the like. Such harsh conditions can be generated during manufacture and/or ordinary use of the antimicrobial glass articles. By way of illustration of the former, harsh conditions can be generated during the formation of any optional additional layers disposed on the surface of the glass substrate (e.g., during polymerization of a fingerprint- and/or smudge-resistant coating on the surface of the glass substrate at elevated temperatures, during direct bonding of adhesives used to adhere the glass substrate to another device, during sputtering of a transparent electrode, during thermal curing of an ink layer, and/or the like), during any intermediate treatment steps (e.g., during plasma cleaning, during chemical etching, during annealing, during chemical cleaning, and/or the like), or the like. Thus, in certain implementations, the antimicrobial glass articles exhibit improved discoloration resistance relative to existing antimicrobial glass articles when exposed to any of the above conditions.

While discoloration resistance can appear to be a qualitative and potentially subjective characterization, there are a number of quantifiable indications of discoloration resistance, examples of which will now be described.

One quantifiable indication of this improved resistance to discoloration can be seen in the change in the optical transmittance that is observed over time. This change can be measured after the formation of the antimicrobial silver-containing region but before the glass article is exposed to any harsh conditions and after the glass article is exposed to harsh conditions. In general, the optical transmittance of the glass articles described herein can be substantially similar both before and after exposure to harsh conditions. In certain implementations, the change in the transmittance of the glass articles described herein after exposure to harsh conditions can be about ±3%. In other implementations, the change in the transmittance of the glass articles described herein after exposure to harsh conditions can be about ±0.5%.

Another quantifiable indication of improved resistance to discoloration is the change in absorbance at about 430 nm, which corresponds to the plasmon resonance associated with the formation of metallic silver nanoparticles (from cationic silver species) in the glass substrate, over time. This change can be measured after the formation of the antimicrobial silver-containing region but before the glass article is exposed to any harsh conditions and after the glass article is exposed to harsh conditions. In general, the absorbance at about 430 nm of the glass articles described herein can be substantially similar both before and after exposure to harsh conditions. In certain implementations, the change in the absorbance at about 430 nm of the glass articles described herein after exposure to harsh conditions can be about ±25%. In other implementations, the change in the absorbance at about 430 nm of the glass articles described herein after exposure to harsh conditions can be about ±10%.

Yet another quantifiable indication of the improved resistance to discoloration is the change in haze that is observed over time. This change can be measured after the formation of the antimicrobial silver-containing region but before the glass article is exposed to any harsh conditions and after the glass article is exposed to harsh conditions. In general, the overall haze of the glass articles described herein after exposure to harsh conditions can be substantially similar to the haze of the as-produced glass articles. In certain implementations, the change in the haze of the glass articles described herein after exposure to harsh conditions can be about ±5%. In other implementations, the change in the haze of the glass articles described herein after exposure to harsh conditions can be about ±2%.

Still another quantifiable indication of the improved resistance to discoloration is the change in CIE 1976 color space coordinates that is observed over time. This change can be measured after the formation of the antimicrobial silver-containing region but before the glass article is exposed to any harsh conditions and after the glass article is exposed to harsh conditions. In general, the individual coordinates (i.e., L*, a*, and b*) of the glass articles described herein after exposure to harsh conditions can be substantially similar to the individual coordinates of the as-produced glass articles. In certain implementations, the change in the L*, a*, and b* coordinates of the glass articles described herein after exposure to harsh conditions can be about ±0.2, ±0.1, and ±0.1, respectively. In other implementations, the change in the L*, a*, and b* coordinates of the glass articles described herein after exposure to harsh conditions can be about ±0.1, ±0.05, and ±0.05, respectively.

The antimicrobial activity and efficacy of the antimicrobial glass articles described herein can be quite high. The antimicrobial activity and efficacy can be measured in accordance with Japanese Industrial Standard JIS Z 2801 (2000), entitled "Antimicrobial Products—Test for Antimicrobial Activity and Efficacy," the contents of which are incorporated herein by reference in their entirety as if fully set forth below. Under the "wet" conditions of this test (i.e., about 37° C. and greater than 90% humidity for about 24 hours), the antimicrobial glass articles described herein can exhibit at least a 5 log reduction in the concentration (or a kill rate of 99.999%) of at least *Staphylococcus aureus, Enterobacter aerogenes*, and *Pseudomonas aeruginosa* bacteria. In certain implementations, the antimicrobial glass articles described herein can exhibit at least a 7 log reduction in the concentration of any bacteria to which it is exposed under these testing conditions.

In scenarios where the wet testing conditions of JIS Z 2801 do not reflect actual use conditions of the antimicrobial glass articles described herein (e.g., when the glass articles are used in electronic devices, or the like), the antimicrobial activity and efficacy can be measured using "drier" conditions. For example, the glass articles can be tested between about 23 and about 37° C. and at about 38 to about 42% humidity for about 24 hours. Specifically, 5 control samples and 5 test samples can be used, wherein each sample has a specific inoculum composition and volume applied thereto, with a sterile coverslip applied to the inoculated samples to ensure uniform spreading on a known surface area. The covered samples can be incubated under the conditions described above, dried for about 6 to about 24 hours, rinsed with a buffer solution, and enumerated by culturing on an agar plate, the last two steps of which are similar to the procedure employed in the JIS Z 2801 test. Using this test, the antimicrobial glass articles described herein can exhibit at least a 1 log reduction in the concentration (or a kill rate of 90%) of at least *Staphylococcus aureus* bacteria and at least a 2 log reduction in the concentration (or a kill rate of 99.99%) of at least *Enterobacter aerogenes*, and *Pseudomonas aeruginosa* bacteria. In certain implementations, the antimicrobial glass articles described herein can exhibit at least a 3 log reduction in the concentration of any bacteria to which it is exposed under these testing conditions.

In other scenarios where the wet testing conditions of JIS Z 2801 do not reflect actual use conditions of the antimicrobial glass articles described herein (e.g., when the glass articles are used in electronic devices, or the like), the antimicrobial activity and efficacy can be measured using "dry" conditions. These conditions described herein are collectively referred to herein as a "Dry Test". The antimicrobial glass articles may exhibit at least a 1 log reduction in the concentration (or a kill rate of 90%) or even at least a 2 log reduction in the concentration (or kill rate of 99%) of at least *Staphylococcus aureus, Enterobacter aerogenes*, and *Pseudomonas aeruginosa* bacteria when tested under the Dry Test, which is described in U.S. Provisional Patent Application No. 61/908,401, which is hereby incorporated by reference in its entirety as if fully set forth below. Under the Dry Test, an inoculum is prepared as follows: inoculating nutrient agar with a portion of a stock having a plurality of bacterial organisms to form a culture, incubating the culture to form a first incubated culture, incubating a portion of the first incubated culture with nutrient agar to form a second incubated culture, incubating a portion of the second incubated culture with nutrient agar to form a third incubated culture, incubating the third incubated culture for approximately 48 hours to form an inoculated test plate with a plurality of bacterial colonies, and suspending a portion of the plurality of bacterial colonies in a buffered test solution of Minimum Essential Medium solution with 15% Fetal Bovine Serum (FBS), adjusting the test solution to a pH of approximately 7 to 8, and adding an organic soil serum at a concentration of approximately 10% to 30% by weight to the test solution. Each of the samples is innoculated with the inoculum and incubated for about 2 hours. Each sample is then washed in a neutralizing solution to form a residual test inoculum. The number of surviving bacterial colonies per volume in the residual test inoculum is then counted to calculate the percent reduction in the number of surviving bacterial colonies in the residual test inoculum (relative to a control residual inoculum).

In a specific embodiment that might be particularly advantageous for applications such as touch accessed or operated electronic devices, an antimicrobial glass article is formed from a chemically strengthened (ion exchanged) alkali aluminosilicate flat glass sheet. The average thickness of the glass sheet is less than or equal to about 1 mm, the average DOL of the ion exchanged compressive stress layer on each major surface of the glass sheet may be about 40 micrometers (μm) to about 100 micrometers (μm), and the average CS across the depth of the compressive stress layer on each major surface may be about 400 MPa to about 1.1 GPa. The average thickness of the antimicrobial silver-containing region, which is formed by a second ion exchange step that occurs after compressive stress layer is formed, may be about 500 nanometers (nm) to about 10 micrometers (μm). A silver concentration of about 30 wt % to about 40 wt % can be attained in the outermost (i.e., closest to the glass substrate surface) 0.01 μm nm of the antimicrobial silver-containing region, based on the total weight of this portion of the antimicrobial silver-containing region. This antimicrobial glass article can have an initial optical transmittance of at least about 90% across the visible spectrum and a haze of less than 1%.

In certain cases, one of the major surfaces of the glass sheet can have an anti-reflection coating and/or an anti-fingerprint coating disposed thereon. After deposition of the anti-reflection coating and/or the anti-fingerprint coating (which can involve temperatures of greater than 200° C., relative humidities of greater than 80%, and exposure to plasma cleaning steps before and/or after deposition), the antimicrobial glass article can have an optical transmittance of at least about 90% across the visible spectrum and a haze of less than 1%. In addition, the change in the L*, a*, and b* coordinates of the glass article after deposition of the anti-reflection coating and/or the anti-fingerprint coating (relative to the uncoated article) can be less than about ±0.15, ±0.08, and ±0.08, respectively. Such an antimicrobial glass article can be used in the fabrication of a touch screen display for an electronic device, offering desirable strength, optical properties, antimicrobial behavior, and resistance to discoloration. In addition, such an antimicrobial glass article can exhibit at least a 5 log reduction in the concentration any bacteria to which it is exposed under the testing conditions of JIS Z 2801.

Embodiments of the antimicrobial glass articles described herein exhibit improved mechanical performance. In one or more embodiments, the antimicrobial glass articles exhibits improved average flexural strength as measured by known methods such as ring-on-ring testing performed according to the ASTM C-1499-03 standard test method for Monotonic Equibiaxial Flexural Strength of Advanced Ceramics at Ambient Temperatures. As used herein, the term "average flexural strength" is intended to refer to the flexural strength of the glass article, as tested through methods such as ring-on-ring testing. The term "average" when used in connection with average flexural strength or any other property is based on the mathematical average of measurements of such property on at least 5 samples, at least 10 samples or at least 15 samples or at least 20 samples. Average flexural strength may refer to the scale parameter of two parameter Weibull statistics of failure load under ring-on-ring testing. This scale parameter is also called the Weibull characteristic strength, at which the failure probability of a brittle material is 63.2%.

The improved average flexural strength may be attributed to higher surface compressive stress values in the antimicrobial glass articles. The compressive stress of the antimicrobial glass articles described herein also decreases from its highest value at the surface along the compressive stress layer monotonically, as described herein.

Compressive stress and DOL are measured using those means known in the art. Such means include, but are not limited to, measurement of surface stress (FSM) using commercially available instruments such as the FSM-6000, manufactured by Luceo Co., Ltd. (Tokyo, Japan), or the like, and methods of measuring compressive stress and depth of layer are described in ASTM 1422C-99, entitled "Standard Specification for Chemically Strengthened Flat Glass," and ASTM 1279.19779 "Standard Test Method for Non-Destructive Photoelastic Measurement of Edge and Surface Stresses in Annealed, Heat-Strengthened, and Fully-Tempered Flat Glass," the contents of which are incorporated herein by reference in their entirety. Surface stress measurements rely upon the accurate measurement of the stress optical coefficient (SOC), which is related to the birefringence of the glass. SOC in turn is measured by those methods that are known in the art, such as fiber and four point bend methods, both of which are described in ASTM standard C770-98 (2008), entitled "Standard Test Method for Measurement of Glass Stress-Optical Coefficient," the contents of which are incorporated herein by reference in their entirety, and a bulk cylinder method.

Various embodiments are further clarified by the following examples.

EXAMPLE 1

Fifteen samples according Example 1A, and fourteen samples each according to Comparative Examples 1B and 1C were prepared by providing identical aluminosilicate glass substrates having the same composition and a thickness of 1 mm. Compressive stress layers were formed in each of glass substrates by immersing the glass substrates in a molten salt bath having the compositions shown in Table 1, for 150 minutes. The molten salt baths had the same temperature of about 420° C.

TABLE 1

Molten salt bath composition for forming the compressive stress layer.

| Examples | % by weight of KNO3 | % by weight of NaNO3 |
|---|---|---|
| Example 1A | 95% | 5% |
| Comparative Example 1B | 100% | 0% |
| Comparative Example 1C | 100% | 0% |

The samples of Comparative Example 1B were not further processed and did not include an antimicrobial silver-containing region. Antimicrobial silver-containing regions were formed in each of the samples of Example 1A and Comparative Example 1C by immersing the glass substrates (having a compressive stress layer) in a silver-containing molten salt bath having the same composition of 0.5 wt % $AgNO_3$ and 99.5 wt % $KNO_3$ for 5 minutes. The temperature of the silver-containing molten salt bath was 350° C.

The surface compressive stress of the samples according to Example 1A and Comparative Example 1B was evaluated using the commercially available FSM-6000 instrument, manufactured by Luceo Co., Ltd. (Tokyo, Japan), and using the methods of measuring compressive stress and depth of layer are described in ASTM 1422C-99, entitled "Standard Specification for Chemically Strengthened Flat Glass," and ASTM 1279.19779. The surface compressive stress and DOL values of the compressive stress layer are provided in Table 2.

TABLE 2

Compressive stress and DOL measurements for Examples 1A and Comparative Examples 1B.

| Examples | Compressive Stress (MPa) | DOL (μm) |
|---|---|---|
| Example 1A | 798 | 47 |
| Comparative Example 1B | 920 | 48 |

The samples according to Example 1A and Comparative Example 1B and 1C were evaluated for average flexural strength, which was plotted in the Weibull plot shown in FIG. 1. The ring-on-ring tests were generally performed according to the ASTM C-1499-03 standard test method for Monotonic Equibiaxial Flexural Strength of Advanced Ceramics at Ambient Temperatures, with a few modifications to test fixtures and test conditions as outlined in U.S. Patent Publication No. 2013/0045375, at [0027], incorporated by reference herein. Note that the samples tested to generate the data depicted in FIG. 1 were not abraded prior to ROR testing.

EXAMPLE 2

Figure 2:
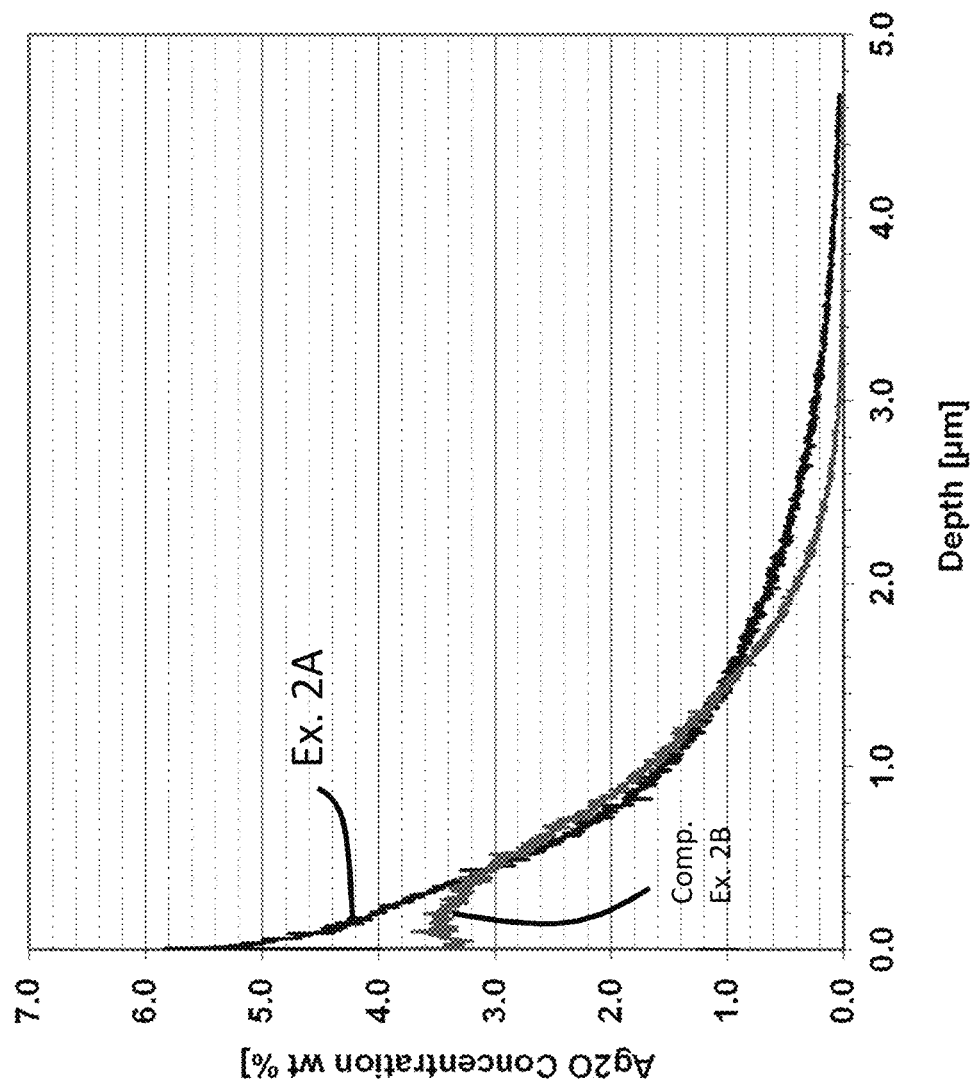
FIG. 2 is a graph showing the silver concentration profile as a function of depth of Example 2A and Comparative Example 2B.

Example 2A was prepared in the same manner as Example 1A above. Comparative Example 2B was prepared in the same manner as Comparative Example 1C. The same substrates were used to form Example 2A and Comparative Example 2B. The silver concentration of each of Example 2A and Comparative Example 2B was evaluated using Secondary ion mass spectrometry (SIMS). As shown in FIG. 2, Example 2A included a higher silver concentration (i.e. above 5 wt. %) at the surface than Comparative Example 2B (i.e., less than about 3.5%), with nearly equivalent silver concentration along the antimicrobial silver-containing region.

EXAMPLE 3

Example 3A was prepared in the same manner as Example 1A above. Comparative Example 3B was prepared in the same manner as Comparative Example 1C. The same substrates having at thickness of about 1 mm, were used to form Example 3A and Comparative Example 3B. The compressive stress profile of Example 3A and Comparative Example 3B were evaluated using FSM and linear interpolation. Other information determined is provided in Table 3.

TABLE 3

Compressive stress profile information for Example 3A and Comparative Example 3B.

| | Example 3A | Comparative Example 3B |
|---|---|---|
| DOL (μm) | 53.0296 | 37.2942 |
| Surface Compressive Stress (MPa) | 790.9707 | 672.4102 |
| CT (estimated) | 20.7578 | 32.5191 |

Figure 3A:
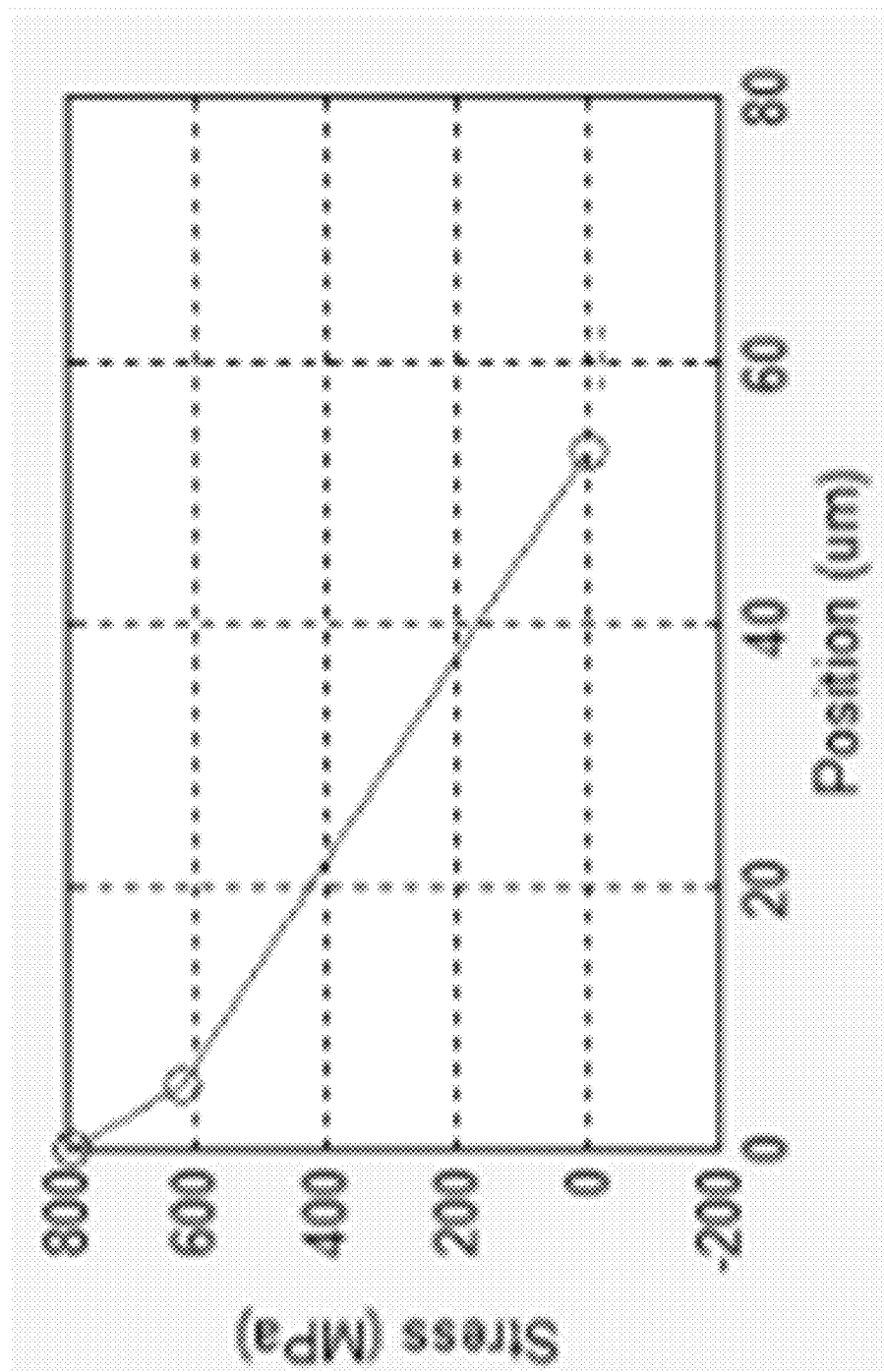
FIG. 3A is a graph showing the compressive stress profile as a function of depth of Example 3A.
Figure 3B:
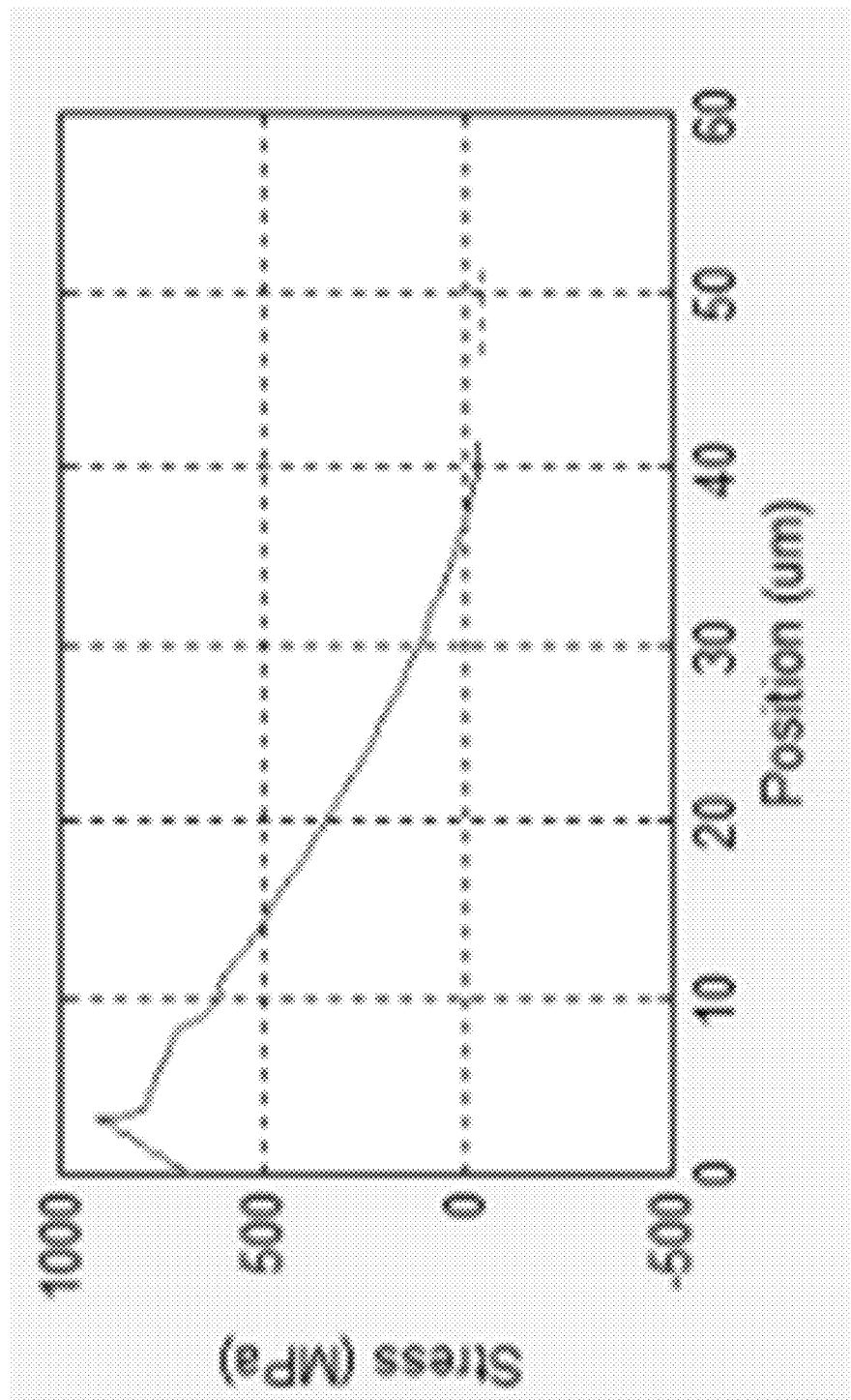
FIG. 3B is a graph showing the compressive stress profile as a function of depth of Comparative Example 3B.

The stress profiles are shown in FIGS. 3A and 3B. As shown in FIGS. 3A and 3B, the compressive stress profile analysis suggests that the use of a poisoning component to form the compressive stress layer and then forming the antimicrobial silver-containing region, provides an increase in surface compressive stress. The compressive stress also decreases monotonically along the compressive stress layer to the DOL.

EXAMPLE 4

Comparative Examples 4A-4B and Example 4C were prepared by providing identical aluminosilicate glass substrates having the nominal composition including about 58 mol % $SiO_2$, about 16.5 mol % $Al_2O_3$, about 17 mol % $Na_2O$, about 2.8 mol % MgO, about 0.05 mol % $SnO_2$ and 6.5 mol % $P_2O_5$. The glass substrates had the same thickness. Comparative Example 4A was prepared by immersing the glass substrate in a molten salt bath including 100% $KNO_3$, having a temperature of 420° C. for 2.5 hours to form a compressive stress layer and then the glass substrate with the compressive stress layer was immersed in a molten salt bath including 80% $KNO_3$ and 20% $AgNO_3$, having a temperature of 350° C. for 5 minutes. Comparative Example 4B was prepared by immersing the glass substrate in a molten salt bath including 100% $KNO_3$, having a temperature of 420° C. for 2.5 hours to form a compressive stress layer and then the glass substrate with the compressive stress layer was immersed in a molten salt bath including 99.5% $KNO_3$ and 0.5% $AgNO_3$, having a temperature of 350° C. for 5 minutes. Example 4C was prepared by immersing the glass substrate in a molten salt bath including 95% $KNO_3$ and 5% $NaNO_3$, having a temperature of 420° C. for 2.5 hours to form a compressive stress layer and then the glass substrate with the compressive stress layer was immersed in a molten salt bath including 99.5% $KNO_3$ and 0.5% $AgNO_3$, having a temperature of 350° C. for 5 minutes. The samples were tested for ring-on-ring characteristic failure load, in the same manner as Example 1. The results of the testing are provided in Table 4.

TABLE 4

Compositions of Molten salt baths and ring-on-ring characteristic failure load.

| Examples | First molten Bath | Second molten bath | Ring-on-Ring Characteristic Failure load |
|---|---|---|---|
| Comparative Example 4A | 100% KNO$_3$ | 80% KNO$_3$, 20% AgNO$_3$ | 257 kgf |
| Comparative Example 4B | 100% KNO$_3$ | 99.5% KNO$_3$, 0.5% AgNO$_3$ | 400 kgf |
| Example 4C | 95% KNO$_3$, 5% NaNO$_3$ | 99.5% KNO$_3$, 0.5% AgNO$_3$ | 483 kgf |

Figure 4:
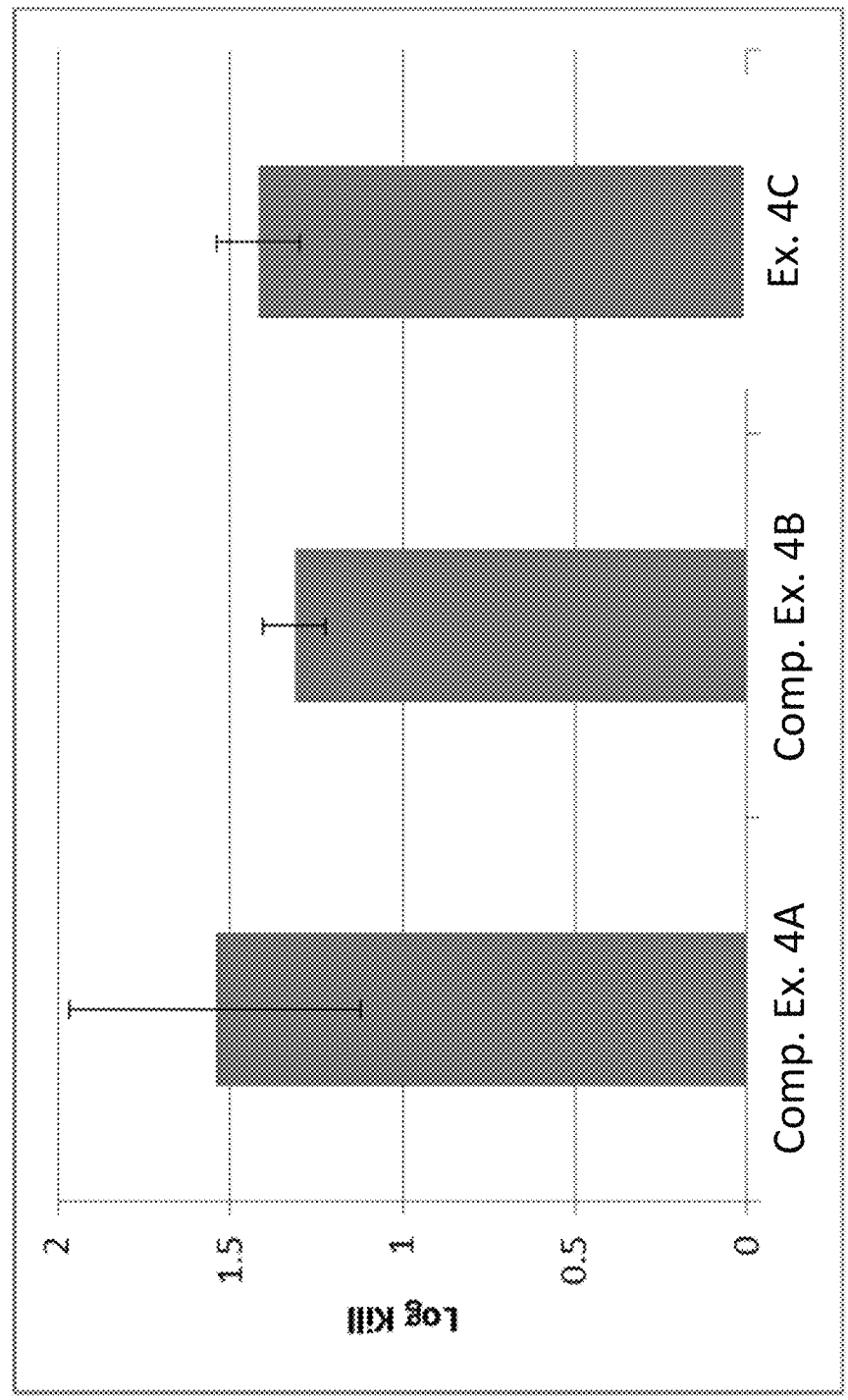
FIG. 4 is a graph showing the antimicrobial efficacy of Comparative Examples 4A-4B and Example 4C.

Comparative Examples 4A and 4B and Example C were tested for antimicrobial efficacy using the same test. As shown in FIG. 4, all three of Comparative Examples 4A-4B and Example 4C performed similarly in terms of antimicrobial efficacy; however, Example 4C exhibited improved strength over Comparative Examples 4A and 4B.

EXAMPLES 5-42

Examples 5-10 were prepared by providing identical aluminosilicate glass substrates having the nominal composition including about 60.9 mol % SiO$_2$, 15.4 mol % Al$_2$O$_3$, 4.9 mol % P$_2$O$_5$, 15.8 mol % Na$_2$O, 2.9 mol % MgO, and 0.1 mol % SnO$_2$.

The glass substrates were subjected to various treatments to form one or more of a compressive stress layer and an antimicrobial silver-containing region, as shown in Table 5. The 1$^{st}$ molten salt bath used to form the compressive stress layer ("Step 1") had a temperature of about 420° C., while the 2$^{nd}$ molten salt bath used to form the antimicrobial silver-containing region ("Step 2") had a temperature of about 350° C. The substrates were immersed in the 1$^{st}$ molten salt bath for 2.5 hours each. The time the strengthened substrates were immersed in the 2$^{nd}$ molten salt bath varied from 10 to 30 minutes, as shown in Table 5. The resulting properties of Examples 5-42 are provided in Table 6. When comparing Examples 5, 6, and 7 having identical Step 2 ion-exchange conditions, it is shown that examples 6 and 7 that included a NaNO3 poisoning component in Step 1 had a higher surface compressive stress, higher ring-on-ring (ROR) load to failure, and higher ROR performance after a 5 gf indentation with a cube corner, when compared to Example 5 (which was formed without a poisoning component in Step 1). Likewise, Examples 8, 9, and 10 also had identical Step 2 ion-exchange conditions. Examples 9 and 10 were formed using a Step 1 that included use of a NaNO$_3$ poisoning component. Examples 9 and 10 exhibited higher surface compressive stress and higher ROR load to failure when compared to Example 8, which was formed without using a NaNO3 poisoning component in Step 1.

TABLE 5

Formation of Examples 5-10.

| | Step 1 Ion-Exchange at 420° C. | | | Step 2 Ion-Exchange at 350° C. | | | wt % Ag at |
|---|---|---|---|---|---|---|---|
| Example | NaNO$_3$— wt % | KNO$_3$ wt % | IOX time (hrs) | AgNO$_3$ wt % | KNO$_3$ wt % | IOX time (min) | outermost 0.01 μm |
| 5 | 0 | 100 | 2.5 | 10 | 90 | 10 | 23.4 |
| 6 | 5 | 95 | 2.5 | 10 | 90 | 10 | 25.8 |
| 7 | 10 | 90 | 2.5 | 10 | 90 | 10 | 29.2 |
| 8 | 0 | 100 | 2.5 | 5 | 95 | 30 | 23.7 |
| 9 | 5 | 95 | 2.5 | 5 | 95 | 30 | 16.6 |
| 10 | 10 | 90 | 2.5 | 5 | 95 | 30 | 17.1 |

TABLE 6

Properties for Examples 5-10

| Ex. | Surface CS (MPa) | % improvement in surface CS over non-poisoned step 1 | ROR load to failure (kgf) | % improvement in ROR load to failure over non-poisoned Step 1 | 5 gf Cube Corner indent then ROR load to failure (kgf) | % improvement in cube corner ROR load to failure over non-poisoned Step 1 |
|---|---|---|---|---|---|---|
| 5 | 385 | N/A | 240 | N/A | 224.601 | N/A |
| 6 | 444 | 15% | 250 | 4% | 244.157 | 9% |
| 7 | 439 | 14% | 351 | 47% | 240.003 | 7% |
| 8 | 480 | N/A | 259 | N/A | | |
| 9 | 564 | 17% | 282 | 9% | | |
| 10 | 561 | 17% | 386 | 49% | | |

The mechanical properties of Examples 5-10 were evaluated using known techniques. For example, the load to failure of the Examples was tested using ring-on-ring testing, in the same manner as Example 1A and Comparative Examples 1B and 1C. Note that for "Ring-on-Ring" testing results in Table 6, Examples 5-10 were not abraded prior to testing. Examples 5-7 were also subjected ring-on-ring testing in the same manner, after being indented with a cube corner indenter at 5 gf load. The flexural strength after 5 gram force (gf) cube corner indentation may be referred to as "strength after indentation". The indentation is made in the center of a 50 mm×50 mm×1 mm sample and then ROR testing is conducted with the indent centered on the support ring so that the indent is on the tensile side of the specimen during testing. The purpose of the cube corner indent is to create repeatable near surface damage. By creating repeatable near surface damage, the effect of the stress profile can be seen more clearly seen than when testing uncontrolled surface flaws as in the non-abraded, non-indented ROR test.

The surface compressive stress (CS) of the Examples was measured using a known technique using the measurement of surface stress using commercially available instruments such as the FSM-6000, manufactured by Luceo Co., Ltd. (Tokyo, Japan), coupled with an inverse WKB.

While the embodiments disclosed herein have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of the present disclosure or the appended claims.

What is claimed is:

1. A method of making an antimicrobial glass article, the method comprising:
    forming a compressive stress layer that extends inward from a surface of a glass substrate to a first depth; and
    forming an antimicrobial silver-containing region that extends inward from the surface of the glass substrate to a second depth, wherein forming the antimicrobial silver-containing region comprises exchanging a plurality of silver cations in silver-containing medium for a plurality of first cations ions in the glass substrate, wherein the compressive stress layer has a compressive stress at the surface of about 500 MPa or greater, and wherein the compressive stress decreases monotonically from the surface to the the first depth.

2. The method of claim 1, wherein forming the compressive layer comprises immersing the glass substrate in a molten salt bath comprising a poisoning component.

3. The method of claim 2, wherein the poisoning component is present in an amount in the range from about 0.01 wt % to about 10 wt %, based on the total weight of the molten salt bath.

4. The method of claim 2, wherein the poisoning component comprises at least one of a cation having an ionic radius that is smaller than the ionic radius of a potassium cation and a cation that is identical to the first cation.

5. The method of claim 4, wherein the plurality of first cations is present in the glass substrate before or after forming the compressive stress layer.

6. The method of claim 2, wherein the poisoning component comprises at least one of $NaNO_3$ and $LiNO_3$.

7. The method of claim 1, wherein the step of forming the compressive stress layer and the step of forming the antimicrobial silver-containing region occur simultaneously.

8. The method of claim 1, wherein a maximal silver concentration of the antimicrobial silver-containing region occurs at the surface of the glass substrate.

9. The method of claim 1, wherein the antimicrobial silver-containing region comprises a silver concentration of about 5 weight percent or greater, based on a total weight of the antimicrobial silver-containing region.

10. The method of claim 1, wherein the antimicrobial silver-containing region comprises a depth of about 20 μm or less.

11. The method of claim 1, wherein a silver concentration at an outermost 10 nm of the antimicrobial silver-containing region is up to about 45 weight percent, based on a total weight of this outermost 10 nm of the antimicrobial silver-containing region.

* * * * *